United States Patent

Pelzer et al.

[11] Patent Number: 5,585,091
[45] Date of Patent: Dec. 17, 1996

[54] USE OF BENZAZOLES UV ABSORBERS, NEW BENZAZOLES AND A PROCESS FOR THEIR PREPARATION

[75] Inventors: Ralf Pelzer, Fürstenberg; Roland Langner, Bevern; Horst Surburg, Holzminden; Horst Sommer, Holzminden; Alfred Krempel, Holzminden; Rudolf Hopp, Holzminden, all of Germany

[73] Assignee: Haarmann & Reimer GmbH, Holzminden, Germany

[21] Appl. No.: 391,853

[22] Filed: Feb. 22, 1995

[30] Foreign Application Priority Data

Feb. 24, 1994 [DE] Germany .......................... 44 06 024.6
Mar. 22, 1994 [DE] Germany .......................... 44 09 689.5

[51] Int. Cl.⁶ .................... A61K 7/44; A61K 31/42; A61K 31/415; A61K 31/425
[52] U.S. Cl. .................... 424/60; 514/366; 514/375; 514/394
[58] Field of Search .................... 424/59, 60; 548/305.4; 514/366, 375, 394

[56] References Cited

U.S. PATENT DOCUMENTS

| | | | |
|---|---|---|---|
| 2,463,264 | 3/1949 | Graenacher et al. | 260/240 |
| 2,995,540 | 8/1961 | Duennenberger et al. | 260/45.8 |
| 3,536,730 | 10/1970 | Baron et al. | 260/301.2 |
| 3,808,005 | 4/1974 | Willems et al. | 96/76 R |
| 4,065,427 | 12/1977 | Pond et al. | 260/45.8 |
| 4,740,519 | 4/1988 | Shroot et al. | 514/443 |
| 5,319,074 | 6/1994 | Redding | 534/618 |

FOREIGN PATENT DOCUMENTS

| | | |
|---|---|---|
| 676103 | 5/1939 | Germany . |
| 1282855 | 11/1968 | Germany . |
| 2550876 | 5/1976 | Germany . |
| 350763 | 1/1961 | Switzerland . |
| 1198632 | 11/1966 | United Kingdom . |
| 9315712 | 8/1993 | WIPO . |

*Primary Examiner*—C. Warren Ivy
*Assistant Examiner*—Evelyn Huang
*Attorney, Agent, or Firm*—Sprung Horn Kramer & Woods

[57] ABSTRACT

Compounds which, per molecule, contain at least 2 benzazolyl groups are outstandingly suitable as UV absorbers for sunscreen compositions.

5 Claims, No Drawings

USE OF BENZAZOLES UV ABSORBERS, NEW BENZAZOLES AND A PROCESS FOR THEIR PREPARATION

The invention relates to the use of compounds which, per molecule, contain at least two benzazolyl radicals, e.g. at least two benzimidazol-2-yl radicals, as UV absorbers in sunscreen compositions, additionally new benzazoles and a process for their preparation by reaction of difunctional anilines with reactive carboxylic acid derivatives.

Depending on the wavelength, UV rays are designated as UV-A rays (320–400 nm, UV-A-I: 340–400 nm, UV-A-II: 320–340 nm) or UV-B rays (280–320 nm). The following is very generally true: the damaging action of the UV rays on the human skin increases with decreasing wavelength and increasing duration of exposure.

UV rays can thus cause skin damage, it being possible for UV-B radiation to cause sunburn (erythema) up to very severe skin burns. Very frequent and unprotected irradiation of the skin with sunlight also leads to a loss in skin elasticity and to increased wrinkle formation and on the whole to premature ageing of the skin. In extreme cases pathological skin changes up to skin cancer can occur.

The UV-A radiation causes a rapid, weak direct pigmentation of the skin. UV-A rays penetrate into deeper skin layers and there can accelerate the ageing process of the skin. The shorter-wave UV-A II radiation assists the formation of sunburn. The UV-A radiation can furthermore elicit phototonic or photoallergic skin reactions. Confirmed relationships exist between UV-A exposure and increased risk of skin cancer.

According to the position of their absorption maxima, UV absorbers for cosmetic and dermatological preparations are divided into UV-A and UV-B absorbers.

There are a large number of safe and effective UV-B absorbers, such as e.g. isooctyl p-methoxycinnamate, isoamyl p-methoxycinnamate, phenylbenzimidazole Na sulphonate and 3-(4'-methylbenzylidene)-camphor.

The number of UV-A absorbers suitable for the protection of human skin, however, is not only very restricted, but these absorbers are also affected by serious disadvantages:

Dibenzoylmethane derivatives (4-t-butyl-methoxy-dibenzoylmethanes and 4-isopropyl-dibenzoylmethanes) are not very photostable, i.e. their UV-A-protection power rapidly declines during use. Additionally, they only have a restricted solubility in cosmetic oils, which can lead to problems in the formulation of cosmetic preparations. The absorption maximum lies in the less hazardous UV-A-I range. Sunscreen products containing dibenzoylmethane derivatives can additionally leave behind on textiles spots which are extremely difficult to wash out. It is also known that dibenzoylmethanes can favour photosensitization of the skin.

Benzophenones are UV-B and UV-A wide-spectrum absorbers and have only a comparatively low absorption in the shortwave UV-A-II range. Their solubility in cosmetic oils is likewise restricted.

Menthyl-o-aminobenzoate has only a very weak absorption in the UV-A range.

Terephthalylidene-dibornanesulphonic acid has an absorption maximum in the UV-A-I range at 345 nm.

UV-A absorbers are sought which have an absorption maximum in the UV-A-II range and protect from the hazardous short-wave UV-A rays by a strong absorption. In addition, these UV-A absorbers should also fulfil the following criteria: excellent photostability, toxicological and dermatological acceptability, excellent heat stability, very good solubility in cosmetic solvents (oils, water, glycols, alcohol etc.), compatibility with cosmetic bases, pH-stable (4–9), processability into cosmetic formulations without problems and stability under application conditions, compatibility with packaging materials, no staining of textiles, but at least: it must be possible to wash out spots on textiles without problems; as free of colours and of neutral odour as possible, freedom from tackiness and low volatility.

In DRP-676 103, the sodium salt of phenylbenzimidazolesulphonic acid (absorption maximum: 316 nm) and similar compounds are recommended as UV absorbers in sunscreen compositions for the human skin. The compounds described, however, do not have the desired photostability or the desired absorption maximum.

Compounds have now surprisingly been found which not only absorb the hazardous UV rays on account of their absorption maximum in the UV-A-II range, but also have an excellent photostability. If the compounds contain carboxyl and/or sulpho groups, the water solubility increases considerably after neutralization with customary bases (e.g. sodium hydroxide, potassium hydroxide, triethanolamine, monoethanolamine, tetrahydroxypropylethylenediamine, tris-(hydroxymethyl)-aminomethane etc.), which leads to non-problematic incorporation into cosmetic bases. It is to be emphasized that cosmetic or dermatological preparations can also be stably formulated with a low pH (up to pH 4) without crystallization occurring. Preparations having a high UV absorber content (for example up to 20% by weight) are possible. It is noticeable that on addition of a base until a pH of above 10 is achieved a shift in the absorption maximum to the longer-wave range (for example from 335 to 355 nm) occurs. It is thus possible, if required, to move this protective function of the compounds to be used according to the invention into the UV-A-I range.

The invention thus relates to the use of compounds which, per molecule, contain at least two benzazolyl groups, as UV absorbers in sunscreen compositions, preferably in cosmetic and dermatological preparations.

Suitable benzazolyl groups are, for example, benzothiazolyl groups, preferably benzoxazolyl groups and in particular benzimidazolyl groups. The expression "at least two benzazolyl groups" should be complied with in the sense of the invention, however, even in the presence of a benzodiazolylene group, i.e. compounds having a benzodiimidazolylene group would be utilizable, for example, according to the invention. An example of such a compound would be e.g. the compound of the formula

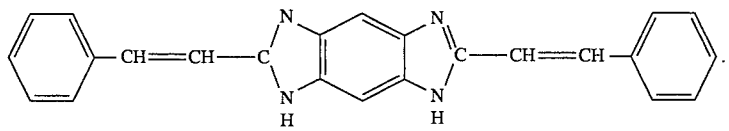

Compounds preferably to be used correspond to the formula

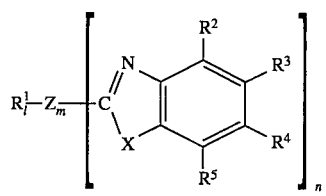

in which

Z denotes a (1+n)-valent organic radical having one or more double bonds in such a position that they complete the double bond systems of at least 2 of the radicals in square brackets to give a conjugated total system, and X denotes S, preferably O, in particular $NR^6$, $R^1$ denotes hydrogen, $C_1$–$C_{18}$-alkyl, $C_1$–$C_4$-alkoxy, $C_5$–$C_{15}$-aryl, $C_2$–$C_{18}$-acyloxy, $SO_3Y$ or COOY, $R^2$ to $R^5$ independently of one another denote nitro or the meaning indicated under $R^1$, $R^6$ denotes hydrogen, $C_1$–$C_4$-alkyl or hydroxy-$C_1$–$C_4$-alkyl, Y denotes hydrogen, Li, Na, K, $NH_4$, ½Ca, ½Mg, ⅓Al or the cation of an organic nitrogen base employed for the neutralization of the free acid groups, l denotes zero or an integer from 1 to 4, m denotes zero or 1 and n denotes an integer from 2 to 6 with the proviso that the sum l+n is at most 6.

Compounds (I) to be used according to the invention are preferably those in which Z denotes a) an olefinically unsaturated aliphatic $C_2$–$C_6$-hydrocarbon radical (which can be interrupted by a $C_5$–$C_{12}$-arylene radical or a $C_4$–$C_{10}$ hetarylene radical), such as e.g. —CH=CH—, —CH=CH—CH=CH— or

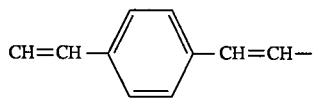

b) a $C_5$–$C_{15}$-arylene radical which can be interrupted by an olefinically unsaturated aliphatic $C_2$–$C_6$-hydrocarbon radical, such as e.g. phenylene, biphenylene, naphthylene,

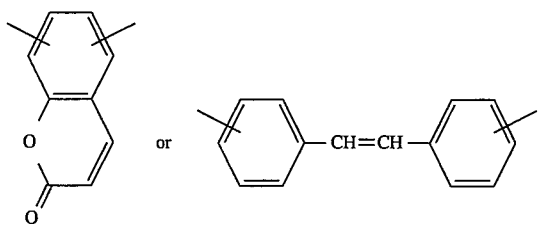

c) a $C_3$–$C_{10}$-hetarylene radical, such as e.g.

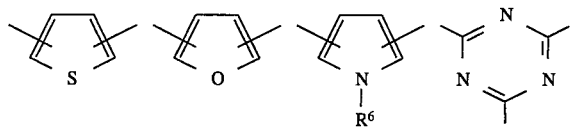

in which $R^6$ has the meaning indicated above, it being possible for the radicals indicated under a) to c) to be substituted by $C_1$–$C_6$-alkyl, $C_1$–$C_6$-alkoxy, phenoxy, hydroxyl, or methylenedioxy groups or amino groups which can be substituted by 1 or 2 $C_1$–$C_5$-alkyl radicals.

Compounds (I) to be used according to the invention are in particular those in which Z represents —CH=CH—, —CH=CH—CH=CH=CH—, or

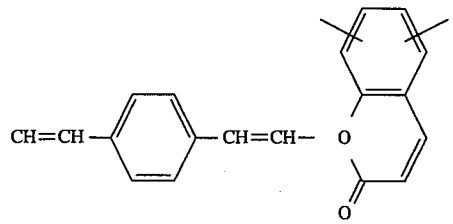

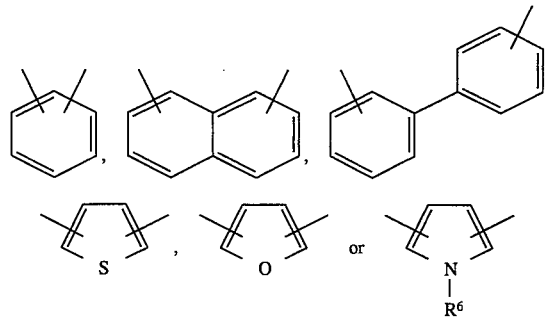

Compounds (I) to be used according to the invention are in particular the following:

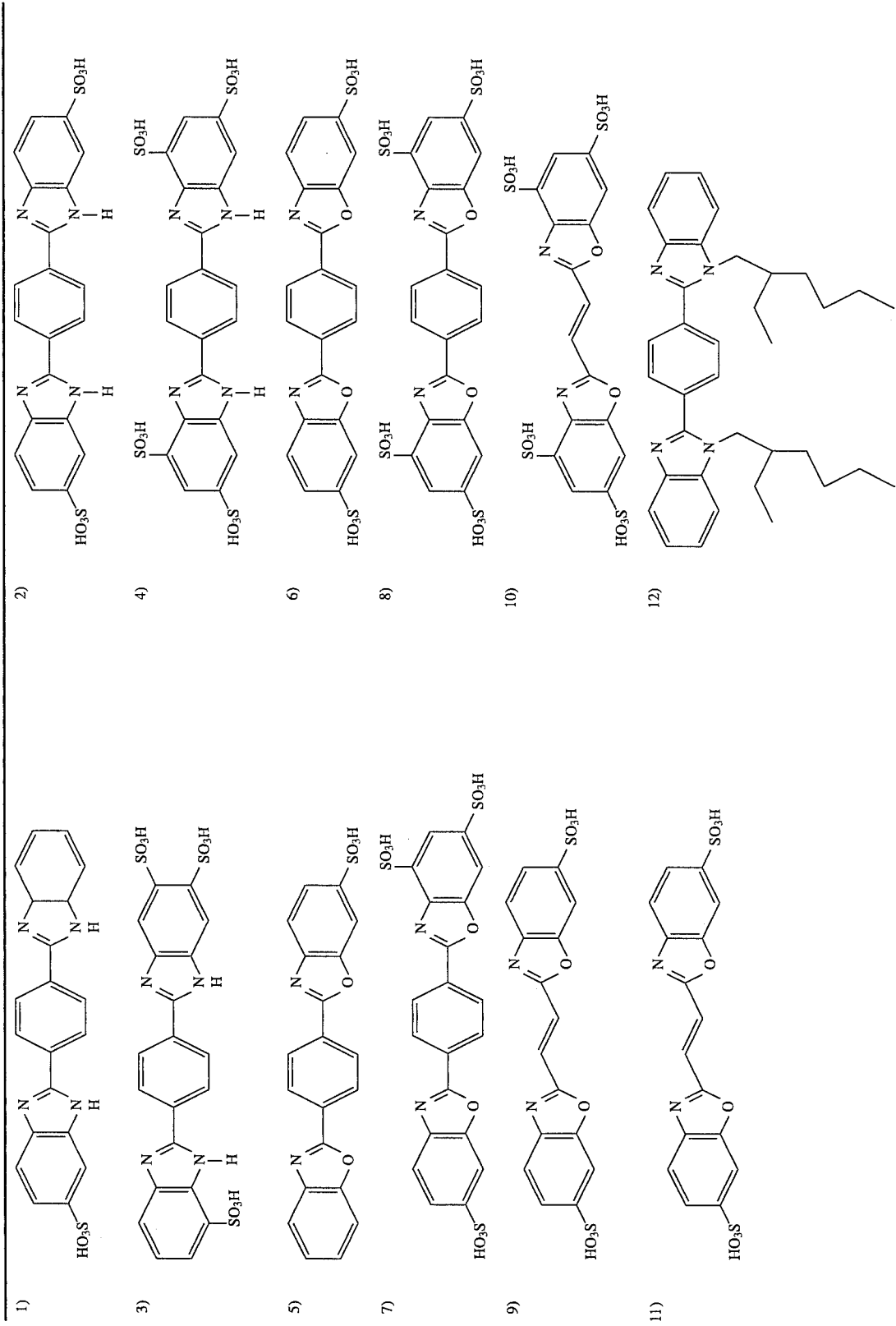

-continued
13) 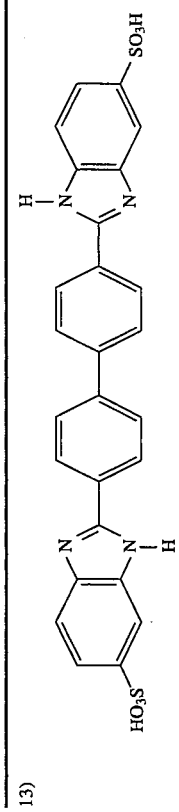
14) 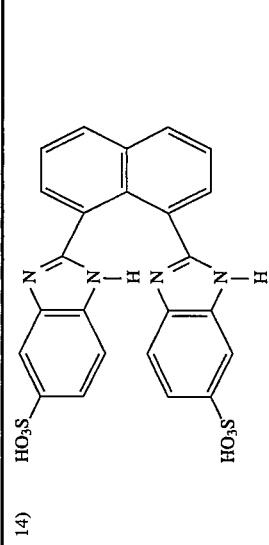
15) 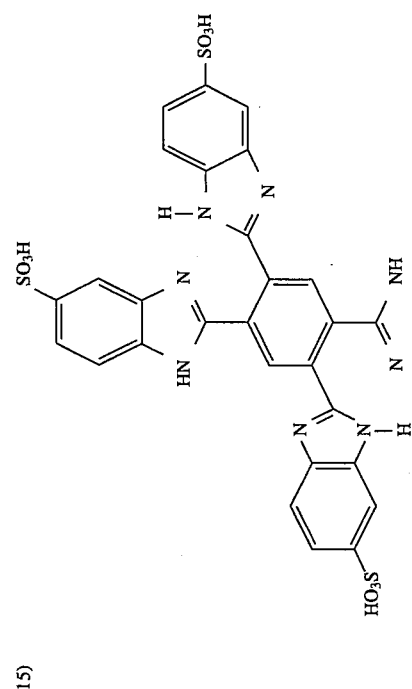
16) 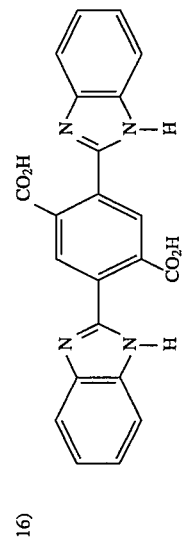
17) 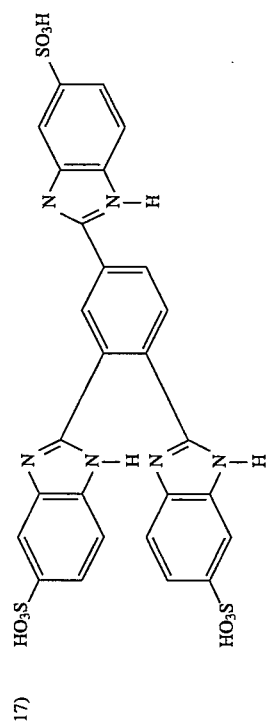
18) 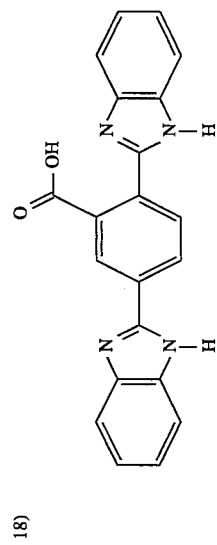

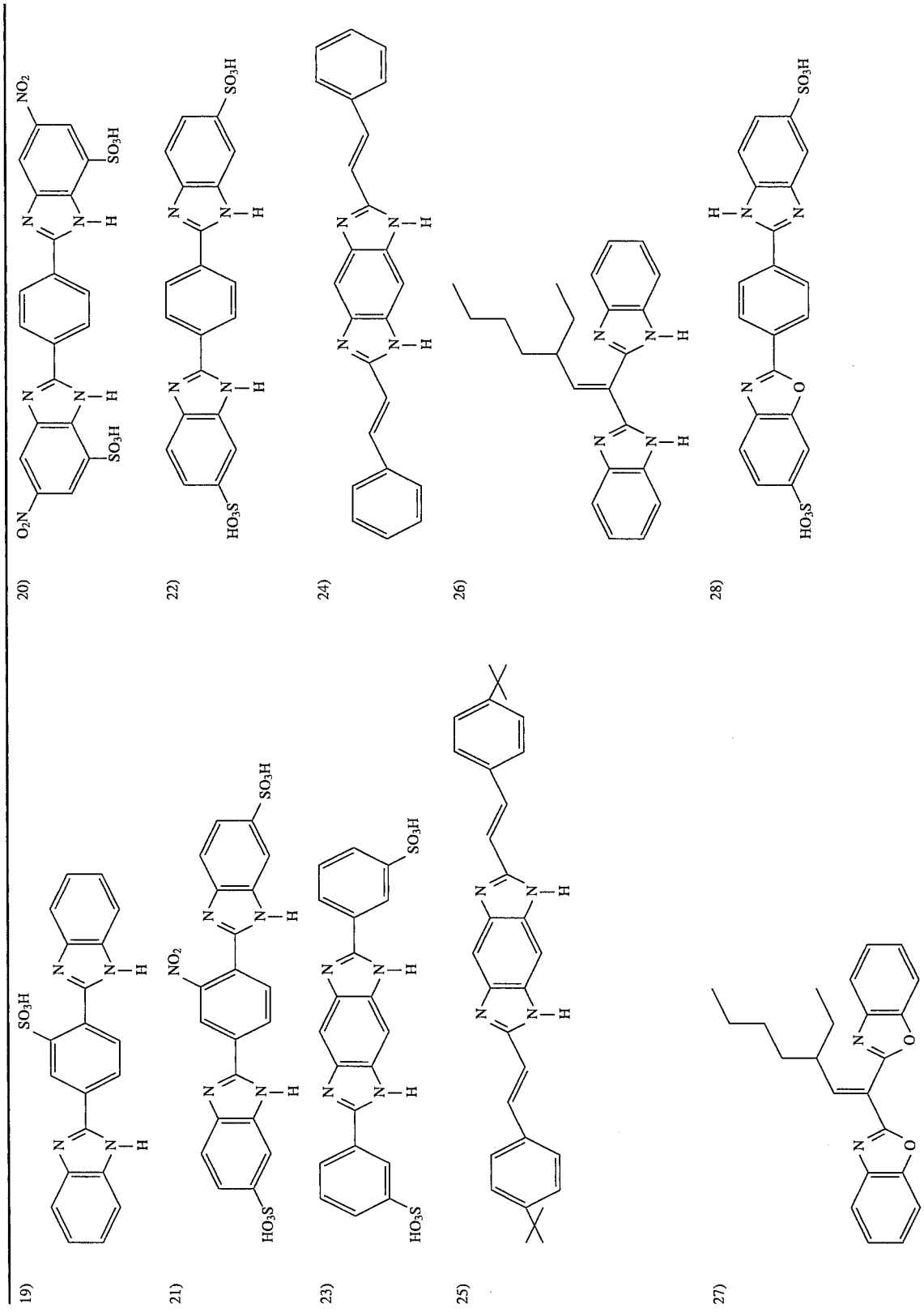

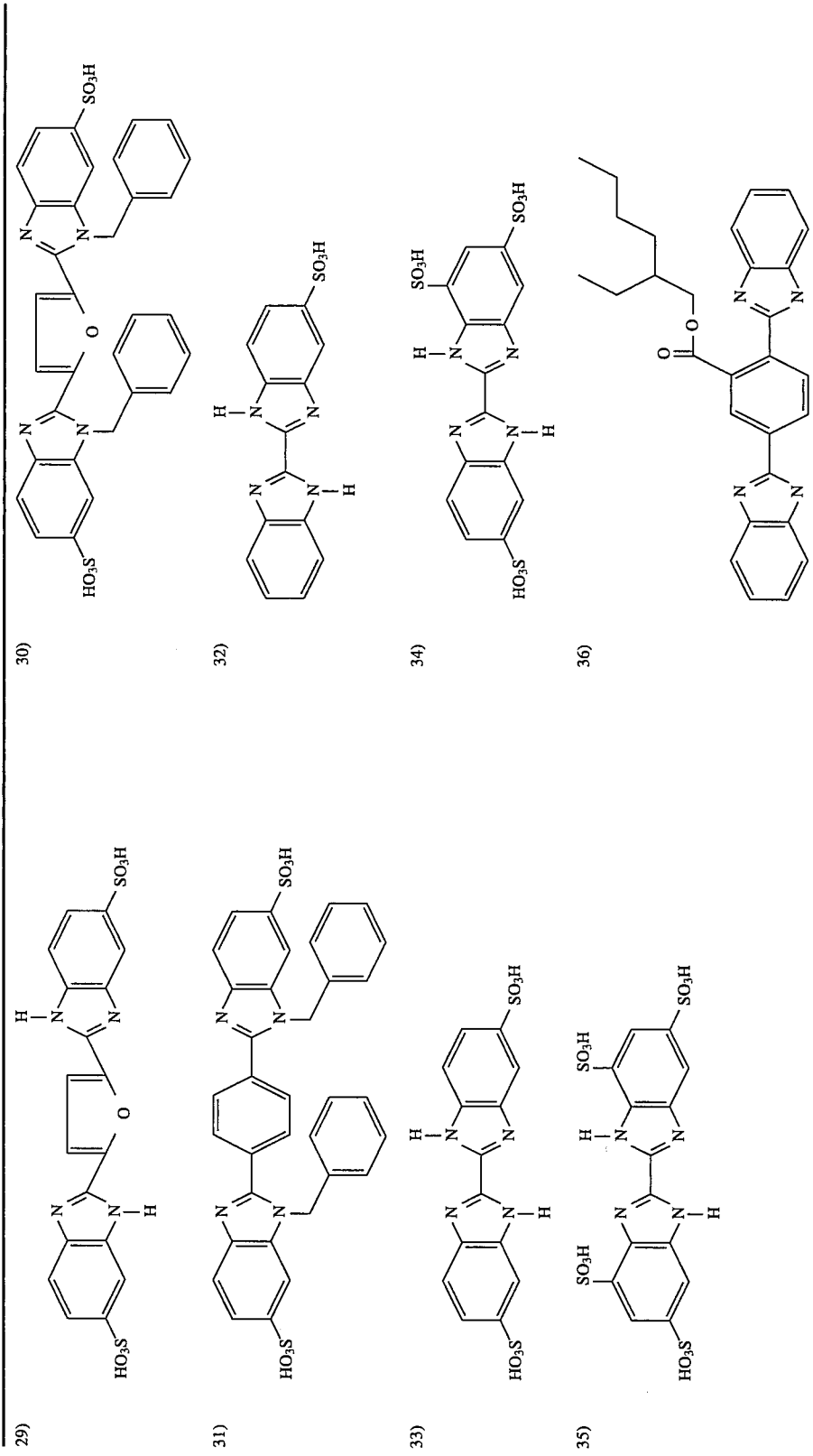

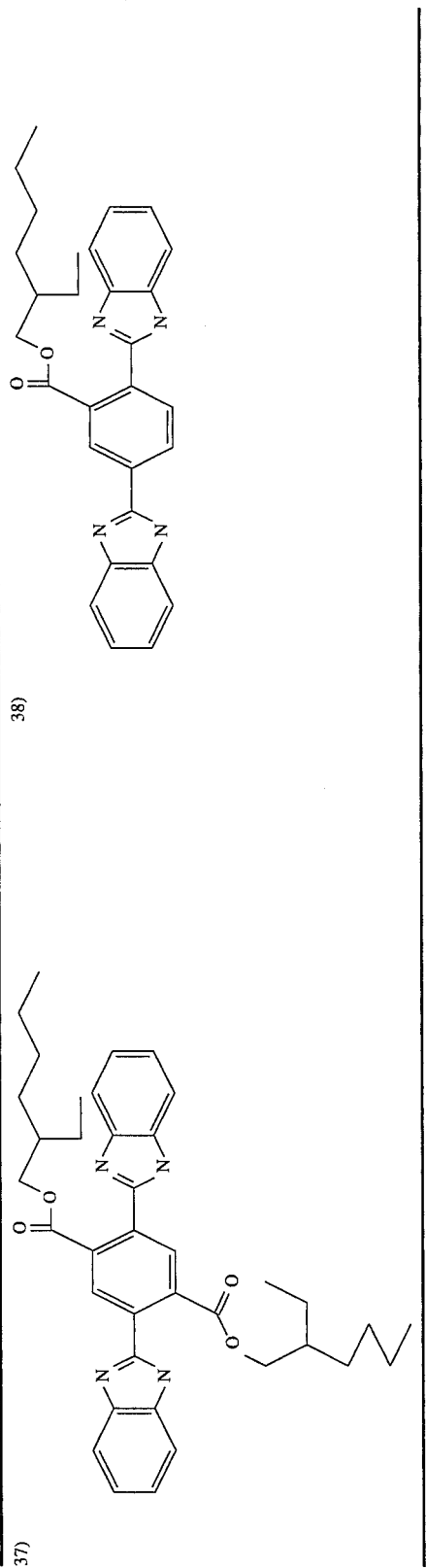

Pharmaceutically utilizable benzazolyl compounds having only one benzazolyl group are known, for example, from German Offenlegungsschrift 35 33 308. They are recommended, inter alia, for loss of hair, for the control of skin diseases and greasy appearance of the skin, for the control of dry skin and for the treatment of detrimental effects of the sun. Prophylactic use against the damaging effect of UV rays on human skin, however, is not mentioned.

The compounds to be used according to the invention are known in some cases; but the use according to the invention was not suggested. Thus U.S. Pat. No. 2,463,264, for example, describes the use of a few compounds, which come under the definition I, as optical brighteners. Use against the damaging effect of UV rays on the human skin is also neither mentioned nor suggested here.

The invention further relates to compounds II of the formula (I) with the proviso that these compounds II contain 1, 3 or 4 $SO_3Y$ groups per molecule.

The compounds I can be prepared by known processes or analogously to these known processes. One of the possible process variants is the reaction of carboxylic acid derivatives with o-phenylenediamine, o-aminophenol or o-aminothiophenol at relatively high temperatures in high-boiling aromatics, such as e.g. diphenyl ether and/or biphenyl, or in inorganic acids such as phosphoric acid or sulphuric acid. Sulphonic acid groups can either be introduced before condensation by sulphonation of the aromatic amines or after condensation by treatment with oleum, hot sulphuric acid or chlorosulphonic acid. According to another process variant, aldehydes are reacted with the aromatic amines under oxidative conditions.

According to a preferred embodiment, condensation and sulphonation are accomplished in a single step: chlorosulphonic acid is reaction medium and reagent at the same time. The invention thus further relates to a process for the preparation of the compounds II by reaction of compounds of the formula

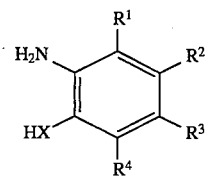

in which

X and $R^1$ to $R^4$ have the meaning indicated above, but $R^1$ and $R^4$ denote neither COOY nor $SO_3Y$, with a compound of the formula

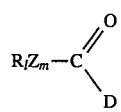

in which

D represents —OH, —$NH_2$, —Cl or O—$C_1$-$C_3$-alkyl, in chlorosulphonic acid at temperatures from 20° to 190° C.

The compounds to be used according to the invention can be used as UV absorbers in cosmetic or dermatological preparations in amounts which prevent the passage of the UV rays through the film of the preparation applied. This is the case if the cosmetic or dermatological preparations contain 0.5 to 15, preferably 1 to 10, in particular 3 to 8% by weight, based on the total weight of the preparation, of the compound to be used according to the invention.

The preparations containing compounds to be used according to the invention can be used for the protection of the skin and the hair—in particular hair already previously damaged by permanent waving, dyeing and bleaching—from UV irradiation. These cosmetic or dermatological preparations serving for the protection of the skin from the UV radiation can be present in the customarily used application forms, i.e. as an oil-in-water or water-in-oil emulsion, as a milk, lotion or cream, aqueous or aqueous-alcoholic gel or lotion, aerosol, hydrodispersion gel (emulsifier-free) or any other customary cosmetic or dermatological preparation. For the protection of the hair from UV rays, preparations are preferably used as a shampoo, rinse, treatments, gels, lotion, spray or cream.

The cosmetic and dermatological preparations can contain the constituents customarily used in these compositions such as e.g. emulsifiers, surface-active compounds, lanolin, petroleum jelly, water, triglycerides of fatty acids, polyethylene glycols, fatty alcohols, ethoxylated fatty alcohols, fatty acid esters (e.g. isopropyl palmitate, isooctyl stearate, diisopropyl adipate etc.), natural or synthetic oils or waxes, pigments (e.g. titanium dioxide, zinc oxide, pearl gloss pigments, colour pigments), thickening agents (e.g. hydroxyethylcellulose, bentonite etc.), preservatives, humectants, vitamins, silicone oils, glycerol, ethyl alcohol and perfume oils.

The compounds to be used according to the invention can be employed in the corresponding preparations as the only UV absorber; but they can also be employed in combination with other UV absorbers—in particular UV-B absorbers, to achieve a UV-A+B wide-spectrum absorption or, with poorly photostable dibenzoylmethane derivatives (e.g. butyl-methoxydibenzoyl-methane or 4-isopropyl-dibenzoylmethane), for their stabilization. Examples of such compounds include p-aminobenzoic acid ethoxylated ethyl p-aminobenzoate (25 mol)

ethylhexyl p-dimethylaminobenzoate n-propoxylated ethyl p-aminobenzoate (2 mol)

glyceryl p-aminobenzoate homomenthyl salicylate 2-ethylhexyl salicylate triethanolamine salicylate 4-isopropylbenzyl salicylate menthyl anthranilate ethyl diisopropylcinnamate 2- ethylhexyl p-methoxycinnamate methyl diisopropylcinnamate isoamyl p-methoxycinnamate p-methoxycinnamic acid diethanolamine salt isopropyl p-methoxycinnamate 2-ethylhexyl 2-cyano-3,3-diphenylacrylate ethyl 2-cyano-3,3-diphenylacrylate 2-phenylbenzimidazolesulphonic acid and salts N,N,N- trimethyl-4-(2-oxoborn-3-ylidenemethyl)-anilinium methylsulphate tetraphthalylidene-dibornanesulphonic acid and salts 4-t-butyl-4'-methoxy-benzoylmethane β-imidazole-4(5)-acrylic acid (urocaninic acid)

2-hydroxy-4-methoxybenzophenone 2-hydroxy-4-methoxybenzophenone-5-sulphonic acid dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methylbenzophenone
α-(2-oxoborn-3-ylidene)-tolyl-4-sulphonic acid and salts
3-(4'-methylbenzylidene)-d,l-camphor
3-benzylidene-d,l-camphor
4-isopropyldibenzoylmethane
2,4,6-trianilino-(p-carbo-2'-ethylhexyl-1'-oxy)-1,3,5-triazine Particularly suitable UV-B absorbers are
2-ethylhexyl p-methoxycinnamate,
isoamyl p-methoxycinnamate,
2-phenylbenzimidazolesulphonic acid and
3-(4'-methylbenzylidene)-d,l-camphor.

The parts indicated in the following examples are parts by weight, and percentage details in each case relate to the weight.

EXAMPLES

Example 1

Phenylenebisbenzimidazoletetrasulphonic acid 108 parts of purified o-phenylenediamine are introduced into 500 parts of conc. $H_2SO_4$ and 800 parts of chlorosulphonic acid are added dropwise. The mixture is heated at 120° C. for 15 min., HCl being continuously released, cooled to 70° C. and treated with 83 parts of terephthalic acid. The reaction mixture again releases HCl and is heated to 180° C. After a reaction time of 30 min. at this temperature, it is cooled to 80° C. and poured onto 2500 parts of ice. The crystallizate precipitated is filtered off, taken up in sodium hydroxide solution and heated with activated carbon. After precipitating with $H_2SO_4$ and drying the crystallizate in vacuo, 299 parts of product are obtained. According to RP-HPLC (MeOH/$H_2O$) this product contains 99% of the title substance and about 1% of the trisulphonic acid. According to NMR, the sulphonic acid groups are in the meta-position relative to one another. (For comparison of the NMR data the pH is to be adjusted unconditionally, as the shift values of the compounds presented here are strongly pH-dependent.) The melting point is >280° C.

$\lambda max_1=208$; $E^{1\%}_{1\ cm}=1142$; $\lambda max_2=256$; $E^{1\%}_{1\ cm}=280.2$; $\lambda max_3=335$; $E^{1\%}_{1\ cm}=745$.

Analogously to this process, the following are employed instead of terephthalic acid:
phthalic acid
isophthalic acid
trimellitic acid
pyromellitic acid

Example 2

Phenylenebisbenzimidazoletrisulphonic acid

If the preparation in Example 1 is followed, but the reaction temperature is kept below 70° C., mainly the trisulphonated product is obtained which, after RP-HPLC isolation, can be characterized by NMR spectroscopy.
$\lambda max_1=206$; $E^{1\%}_{1\ cm}=650$; $\lambda max_2=254$; $E^{1\%}_{1\ cm}=162$; $\lambda max_3=335$; $E^{1\%}_{1\ cm}=756$.

Example 3

Phenylenebisbenzimidazoledisulphonic acid 550 parts of concentrated sulphuric acid (96% strength) are initially introduced and 108 parts of o-phenylenediamine are added gradually. The reaction is exothermic and the mixture heats to 95°–100° C. At this temperature 83 parts of terephthalic acid are added and the mixture is heated at 200° C. for 5 h. After cooling to 100°–120° C., it is poured onto 1000 parts of ice and stirred for 1 h. The green to brown precipitate is filtered off, taken up in NaOH and heated under reflux for 1 h with 20 parts of activated carbon. After filtration, the pH is adjusted to 1.5 to 2 using $H_2SO_4$ and the light precipitate is filtered off. The product is slurried with methanol, filtered off and dried.

$\lambda max_1=218$; $E^{1\%}_{1\ cm}=1057$; $\lambda max_2=256$; $E^{1\%}_{1\ cm}=424$; $\lambda max_3=351$; $E^{1\%}_{1\ cm}=1289$.

Phenylenebisbenzoxazoledisulphonic acid is prepared analogously from o-hydroxyaniline and terephthalic acid.

$\lambda max_1=203$; $E^{1\%}_{1\ cm}=1395$; $\lambda max_2=323$; $E^{1\%}_{1\ cm}=907$; $\lambda max_3=337$; $E^{1\%}_{1\ cm}=897$.

Example 4

2,2'-bisbenzimidazoledisulphonic acid 44 parts of oxamide and 108 parts of o-phenylenediamine are initially introduced into 300 parts of ethylene glycol and heated to reflux. The resulting ammonia gas is absorbed in a wash bottle containing hydrochloric acid. As soon as about 16 parts of ammonia have been absorbed, the reaction mixture is cooled and treated with 100 parts of water. The precipitated product is employed immediately in the next step after filtration and drying.

For this, 23.4 parts of this 2,2'-bisbenzimidazole are dissolved in 100 parts of conc. $H_2SO_4$ and the mixture is treated with 55 parts of fuming (30% strength free $SO_3$) sulphuric acid and heated to 100°–120° C. After 3 h, the mixture is added to 500 parts of ice, a greenish fluorescence becoming discernible. The filtrate is neutralized with sodium hydroxide solution and decolorized with activated carbon. After concentrating the solution and drying, a pale yellow, excellently water-soluble sodium salt of the title compound is obtained, which shows a purplish fluorescence in solution.

Example 5

Sunscreen milk (O/W)

A 20% strength preliminary solution, neutralized with sodium hydroxide, was prepared from a UV-A absorber according to formula (I). 20% of this preliminary solution was employed, which corresponds to an active content of 4.00% of UV-A absorber in the final formulation.

Components used:
Alugel 30 DF: aluminium distearate, supplier 21
Arlacel 581: glyceryl mono- and distearate and polyethylene glycol stearate, supplier 4
Arlacel 165: glyceryl stearate/polyethylene glycol (MW 100) stearate mixture, supplier 4.
Arlamol HD: isohexadecane, supplier 4
Arlatone T: oleate of ethoxylated sorbitol, supplier 5
Arosol: phenoxyethanol, supplier 1
Baysilone Fluid PK 20: silicone oil, supplier 5
Betone Gel MIO: mineral oil, supplier 13
Carbopol 940: polyacrylic acid, supplier 2
Carbopol 941: polyacrylic acid, supplier 2

Carbopol 1342: polyacrylate, supplier 2
Carbopol ETD 2001: acrylic acid copolymer, supplier 2
Cetiol MM: myristyl myristate, supplier 3
Cetiol S: dioctylcyclohexane, supplier 3
Cetiol V: decyl oleate, supplier 3
Cetiol OE: dicapryl ether, supplier 3
Cetiol SN: cetyl/stearyl isononanoate, supplier 3
Cremophor NP 14: nonylphenol etherified with 14 mol of ethylene oxide, supplier 6
Cutina CBS: glyceryl stearate, cetyl/stearyl alcohol, cetyl palmirate, coconut glycerides, supplier 3
Cutina FS 45: palmitic/stearic acid mixture, supplier 3
Cutina MD: glyceryl stearate, supplier 3
Dehymuls HR E 7: ethoxylated hydrogenated castor oil, supplier 3
Dehyquart A: cetyltrimethylammonium chloride, supplier 3
Elfacos C 26: hydroxyoctacosanyl hydroxy-stearate, supplier 19
Elfacos E 200: ethylene glycol/dodecylglycol polyether with methoxy end groups, supplier 19
Elfacos ST 9: ethylene glycol/dodecyl-glycol polyether, supplier 19
Eumulgin B 1: cetyl/stearyl alcohol, etherified with 12 mol of ethylene oxide, supplier 3
Eumulgin B 2: cetyl/stearyl alcohol, etherified with 20 mol of ethylene oxide, supplier 3
Eusolex 6007: octyl N,N-dimethyl-p-aminobenzoate, supplier 17
Euxyl K 100: 5-chloro-2-methyl-4-isothiazolin-3-one, 2-methyl-4-isothiazolin-3-one and benzyl alcohol, supplier 13
Genapol LRO liq.: sodium lauryl sulphate, supplier 12
Heliopan, Type AV: isooctyl p-methoxy-cinnamate, supplier 1
Heliopan, Type E 1000: isoamyl p-methoxycinnamate, supplier 1
Lameform TGI: triglyceryl diisostearate, supplier 3
Lamepon S: protein/coconut fatty acid condensate, potassium salt, supplier 3
Lanette O: cetyl/stearyl alcohol mixture, supplier 3
Mulsifan RT 203/80: fatty alcohol polyglycol ether, supplier 9
Myritol 318: caprylic/capric tri-glyceride, supplier 3
Natrosol 250 HHR: hydroxyethylcellulose, supplier 15
Neo Heliopan, Type BB: 2- hydroxy-4-methoxy-benzophenone, supplier 1
Neo Heliopan, Type Hydro: phenylbenzimidazolesulphonic acid, supplier 1
Neo Heliopan, Type 303: isooctyl α-phenyl-β-cyano-cinnamate, supplier 1
Nutrilan L: protein hydrolysate, Na salt, supplier 3
Permulgin: wax, supplier 18
Phenonip: mixture of p-hydroxybenzoic acids, supplier 11
Protegin WX: combination of non-ionic fatty acid esters of polyhydric alcohols with waxes and purified saturated hydrocarbons, supplier 10
Quarternium-18 Hectorit: propylene carbonate, supplier 13
Solbrol P: propyl p-hydroxybenzoate, supplier 5
Solbrol M: methyl p-hydroxybenzoate, supplier 5
Tagat S: polyoxyethylene glyceryl monostearate, supplier 10
Tegin M: glyceryl stearate, supplier 10
Texapon MG 3: magnesium lauryl sulphate/disodium lauryl sulphosuccinate, supplier 3
Tioveil MOTG: 40% strength by weight aqueous dispersion of titanium dioxide, supplier 20
Trilon B fl.: tetrasodium ethylenediamine-tetraacetates, supplier 6
Uvinul MS 40: p-hydroxybenzophenone, supplier 6
Uvinul P 25: polyethyleneglycol ester of p-aminobenzoic acid, supplier 6
Uvinul T 150: isooctyl triazinyl-p-aminobenzoate, supplier 6
Veegum Ultra: magnesium aluminum silicate, supplier 14

Suppliers
1. Haarmann & Reimer GmbH, Holzminden
2. B. F. Goodrich Comp., Neuss
3. Henkel KGaA, Düsseldorf
4. ICI Speciality Chemicals, Frankfurt
5. Bayer AG, Leverkusen
6. BASF, Ludwigshafen
7. Sutton Lab. Inc., Chatham, N.J., USA
8. Gattefossé, Saint-Priest Cédex
9. Zschimmer & Schwarz GmbH, Lahnstein
10. Goldschmidt AG, Essen
11. Nipa Lab. Ltd., Pontypridd Mid Glam, Wales, GB
12. Hoechst AG, Frankfurt
13. Schülke a Mayr GmbH, Norderstedt
14. R. T. Vanderbilt Company Inc., Norwalk, USA
15. Hercules Inc., Wilmington, Del., USA
16. Givaudan-Route GmbH, Geneva
17. E. Merck, Darmstadt
18. Koster Keunen Holland BY, Bladel, NL
19. Akzo Chemie GmbH, Düren
20. Tioxide Chemicals Ltd., Billingham, Cleveland, GB
21. Chemische Werke Bärlocher, Munich

|   | Constituents | % |
|---|---|---|
| A) | Cutina FS 45 | 2.00 |
|   | Eumulgin B 1 | 0.25 |
|   | Eumulgin B 2 | 0.25 |
|   | Cutina MD | 2.00 |
|   | Lanette O | 2.80 |
|   | Myritol 318 | 5.00 |
|   | Liquid paraffin 65 cp | 3.00 |
|   | Arosol | 0.80 |
|   | Solbrol P | 0.10 |
|   | Isooctyl-p-methoxycinnamate | 3.00 |
|   | Isoamyl p-methoxycinnamate | 3.00 |
|   | Neo Heliopan, type BB | 1.50 |
| B) | Water, dist. | 51.05 |
|   | Carbopol 941 | 0.30 |
|   | Sodium hydroxide, 10% strength in water | 2.45 |
|   | 1,2-Propylene glycol | 2.00 |
|   | Solbrol M | 0.20 |
|   | UV-A absorber according to formula (I), employed as a 20% strength solution after neutralization with sodium hydroxide corresponds to active substance: 4.00% | 20.00 |
| C) | Perfume oil | 0.30 |

Preparation procedure:

Part A: Melt at about 75° to 80° C.

Part B: Disperse Carbopol in the water in lump-free form, neutralize with sodium hydroxide solution, add the residual constituents and heat to about 95° C.

Add part B to part A with stirring and stir while cooling to room temperature. Add part C at about 30° C. Check pH (7.0–7.5).

Example 6

Sunscreen lotion (O/W)

A 20% strength preliminary solution, neutralized with sodium hydroxide, was prepared from the UV absorber according to formula (I). 15% of this solution was employed, which corresponds to an active content of 3.00% of UV-A absorber in the final formulation.

| | Constituents | % |
|---|---|---|
| A) | Arlacel 165 | 3.00 |
| | Eumulgin B 2 | 1.00 |
| | Lanette O | 2.00 |
| | Myritol 318 | 4.00 |
| | Cetiol OE | 6.00 |
| | Betone Gel MIO and Quaternium-18 Hectorite | (3.00) |
| | Phenonip | 0.20 |
| | Cutina CBS | 2.00 |
| | Isooctyl p-methoxycinnamate | 7.00 |
| | 4-Methylbenzylidene-camphor | 1.00 |
| | Zinc oxide neutral H&R | 5.00 |
| B) | Water, dist. | 45.90 |
| | Veegum Ultra | 1.00 |
| | Natrosol 250 HHR | 0.30 |
| | Glycerol 85% | 3.00 |
| | Phenonip | 0.30 |
| | UV-A absorber according to formula (I), employed as a 20% strength solution after neutralization with sodium hydroxide corresponds to active substance: 3.00% | 15.00 |
| C) | Perfume oil | 0.30 |

Preparation procedure:

Part A: Melt at about 80° C., then carefully disperse neutral zinc oxide.

Part B: Heat to about 90° C. without Veegum and Natrosol, then disperse Veegum and Natrosol. Add part B to part A with stirring. Stir while cooling to room temperature.

Part C: Add part C at 30° C. and then homogenize. Check pH (7.0–7.5).

Example 7

Sunscreen cream (O/W)

A 20% strength preliminary solution, neutralized with sodium hydroxide, was prepared from the UV-A absorber according to formula (I). 20% of this preliminary solution was employed, which corresponds to an active content of 4.00% of UV-A absorber in the final formulation.

| | Constituents | % |
|---|---|---|
| A) | Tegin M | 3.00 |
| | Tagat S | 2.30 |
| | Lanette O | 3.50 |
| | Liquid paraffin 65 cp | 4.00 |
| | Arlamol HD | 3.50 |
| | Cetiol MM | 2.00 |
| | Phenonip | 0.20 |
| | Isooctyl p-methoxycinnamate | 4.00 |
| | Isoamyl p-methoxycinnamate | 4.00 |
| B) | Water, dist. | 16.85 |
| | Phenonip | 0.20 |
| | Neo Heliopan, type Hydro, employed as a 15% strength solution after neutralization with sodium hydroxide/phenylbenzimidazole-sulphonic acid corresponds to active substance: 1.00% | 6.70 |
| | UV-A absorber according to formula (I), employed as a 20% strength solution after neutralization with sodium hydroxide corresponds to active substance: 4.00% | 20.00 |
| | 1,2-Propylene glycol | 2.00 |
| C) | Water, dist. | 25.00 |
| | Carbopol 940 | 0.40 |
| | Sodium hydroxide, 10% strength in water | 2.05 |
| D) | Perfume oil | 0.30 |

Preparation procedure:

Part A: Melt at about 80° C.

Part B: Heat to about 90° C. Add part B to part A with stirring. Stir while cooling to room temperature.

Part C: Disperse Carbopol in water in lump-free form, neutralize with sodium hydroxide solution to give a gel, add to parts A/B at about 60° C.

Part D: Perfume the emulsion at about 30° C. Check pH (7.0–7.5).

Example 8

Sunscreen cream (O/W)

A 20% strength preliminary solution, neutralized with sodium hydroxide, was prepared from the UV-A absorber according to formula (I). 25% of this preliminary solution was employed, which corresponds to an active content of 5.00% of UV-A absorber in the final formulation.

| | Constituents | % |
|---|---|---|
| A) | Cutina FS 45 | 2.00 |
| | Eumulgin B 1 | 0.25 |
| | Eumulgin B2 | 0.25 |
| | Cutina MD | 2.00 |
| | Lanette O | 3.00 |
| | Myritol 318 | 5.00 |
| | Cetiol SN | 3.00 |
| | Arosol | 0.80 |
| | Solbrol P | 0.10 |
| | Isoamyl p-methoxycinnamate | 5.00 |
| | Isooctyl p-methoxycinnamate | 3.00 |
| | 4-Methylbenzylidene-camphor | 1.00 |
| | Octyl salicylate | 3.00 |
| | Butylmethoxydibenzoylmethane | 1.00 |
| B) | Dist. water | 40.90 |
| | Carbopol 940 | 0.40 |
| | Sodium hydroxide, 10% strength in water | 1.80 |
| | 1,2-Propylene glycol | 2.00 |
| | Solbrol M | 0.20 |
| | UV-A absorber according to formula (I) employed as a 20% strength solution after neutralization with sodium hydroxide corresponds to active substance 5.00% | 25.00 |
| C) | Perfume oil | 0.30 |

Preparation procedure:

Part A: Melt at about 80° C.

Part B: Disperse Carbopol in water in lump-free form, add remaining constituents and heat to about 90° C. Then add part B to part A with stirring. Stir while cooling to room temperature.

Part C: Perfume the emulsion at about 30° C. Check pH (7.0–7.5).

Example 9

Sunscreen milk (W/O)

A 30% strength preliminary solution, neutralized with triethanolamine, was prepared of the UV-A absorber according to formula (I). 6.7% of this preliminary solution was employed, which corresponds to an active content of 2.00% of UV-A absorber in the final formulation.

|    | Constituents | % |
|----|---|---|
| A) | Lameform TGI | 4.00 |
|    | Dehymuls HR E 7 | 4.00 |
|    | Cetiol S | 12.00 |
|    | Liquid paraffin 65 cp | 8.50 |
|    | Permulgin 3220 | 1.00 |
|    | Isooctyl p-methoxycinnamate | 5.00 |
|    | Isoamyl p-methoxycinnamate | 5.00 |
|    | Isopropyldibenzoylmethane | 1.00 |
| B) | Water, dist. | 49.65 |
|    | 1,2-Propylene glycol | 2.00 |
|    | Triethanolamine | 0.35 |
|    | Phenonip | 0.50 |
|    | UV-A absorber, according to general formula (I), employed as a 30% strength solution after neutralization with triethanolamine corresponds to active substance 2.00% | 6.70 |
| C) | Perfume oil | 0.30 |

Preparation procedure:

Part A: Melt at about 80° C.

Part B: Mix constituents together. Check pH of the water phase (7.0–7.5). Heat to about 90° C. Slowly add part B to part A with stirring. Stir while cooling to room temperature.

Part C: Perfume the emulsion at about 35° C., then homogenize.

Example 10

Sunscreen lotion (W/O)

A 30% strength preliminary solution, neutralized with triethanolamine, was prepared of the UV-A absorber according to formula (I). 20% of this preliminary solution was employed, which corresponds to an active content of 3.00% of UV-A absorber in the final formulation.

|    | Constituents | % |
|----|---|---|
| A) | Elfacos E 200 | 3.00 |
|    | Elfacos ST 9 | 1.00 |
|    | Elfacos C 26 | 1.00 |
|    | Liquid paraffin 65 cp | 6.00 |
|    | Isopropyl diisostearate | 7.00 |
|    | Isooctyl p-methoxycinnamate | 7.00 |
|    | Octyl salicylate | 5.00 |
|    | Tioveil MOTG, 40% strength dispersion | 12.50 |
| B) | Water, dist. | 43.40 |
|    | Trilon B liq. | 0.30 |
|    | 86% Glycol | 3.00 |
|    | Phenonip | 0.50 |
|    | UV-A absorber according to formula (I), employed as a 30% strength solution after neutralization with triethanolamine corresponds to active substance: 3.00 | 10.00 |
| C) | Perfume oil | 0.30 |

Preparation procedure:

Part A: Melt at about 80° C. and stir well.

Part B: Heat to about 90° C. Add part B to part A with stirring. Stir while cooling to room temperature.

Part C: Perfume at about 30° C., then homogenize.

Example 11

Sunscreen cream (W/O)

A 30% strength preliminary solution, neutralized with triethanolamine, was prepared of the UV-A absorber according to formula (I). 10% of this preliminary solution was employed, which corresponds to an active content of 3.00% of UV-A absorber in the final formulation.

|    | Constituents | % |
|----|---|---|
| A) | Protegin WX | 23.00 |
|    | Alugel 30 DF | 0.50 |
|    | Liquid paraffin 34 cp | 3.00 |
|    | Solbrol R | 0.05 |
|    | Isooctyl p-methoxycinnamate | 5.00 |
|    | Neo Heliopan, type 303 | 7.00 |
|    | Menthyl anthranilate | 4.00 |
|    | Eusolex 6007 | 4.00 |
| B) | Water, dist. | 37.30 |
|    | Solbrol M | 0.15 |
|    | Magnesium sulphate | 0.40 |
|    | 70% Sorbitol | 5.00 |
|    | UV-A absorber according to general formula (I), employed as a 30% strength solution after neutralization with triethanolamine corresponds to active substance: 3.00 | 10.00 |
| C) | Perfume oil | 0.30 |

Preparation procedure:

Part A: Dissolve Alugel in liquid paraffin with heating. Add the remaining constituents and melt at about 80° C.

Part B: Heat to about 90° C. Add part B to part A with stirring and stir while cooling to room temperature.

Part C: Perfume the cream at about 30° C. and then homogenize.

Example 12

Sunscreen lotion (W/O)

A 30% strength preliminary solution, neutralized with triethanolamine, was prepared of the UV-A absorber according to formula (I). 10% of this preliminary solution was employed, which corresponds to an active content of 3.00% of UV-A absorber in the final formulation.

|    | Constituents | % |
|----|---|---|
| A) | Arlacel 581 | 3.50 |
|    | Arlatone T | 0.75 |
|    | Cetiol S | 12.00 |
|    | Liquid paraffin 34 cp | 5.50 |
|    | Permulgin 3220 | 1.00 |
|    | Isooctyl p-methoxycinnamate | 5.00 |
|    | Isoamyl p-methoxycinnamate | 5.00 |
|    | Uvinul T 150 | 1.00 |
| B) | Water, dist. | 53.20 |
|    | 1,2-Propylene glycol | 2.00 |
|    | triethanolamine | 0.35 |
|    | Phenonip | 0.40 |
|    | UV-A absorber according to formula (I), employed as a 30% strength solution after neutralization with triethanolamine corresponds to active substance: 3.00 | 10.00 |
| C) | Perfume oil | 0.30 |

Preparation procedure:

Part A: Melt at about 80° C.

Part B: Mix constituents together. Check pH of the water phase (7.0–7.5). Heat to about 90° C. Add part B slowly to part A with stirring. Stir while cooling to room temperature.

Part C: Perfume the emulsion at about 35° C. and then homogenize.

Example 13

Lip protection cream (W/O)

A 30% strength preliminary solution, neutralized with triethanolamine, was prepared of the LTV-A absorber according to formula (I). 10% of this preliminary solution was employed, which corresponds to an active content of 3.00% of UV-A absorber in the final formulation.

|    | Constituents | % |
|----|---|---|
| A) | Protegin WX | 23,00 |
|    | Alugel 30 DF | 0,50 |
|    | Liquid paraffin 34 cp | 5,00 |
|    | Cetiol V | 3,00 |
|    | Solbrol P | 0,05 |
|    | Isooctyl p-methoxycinnamate | 8,00 |
|    | Butylmethoxydibenzoylmethane | 1,00 |
| B) | Water, dist. | 43,30 |
|    | Solbrol M | 0,15 |
|    | Magnesium sulphate | 0,40 |
|    | 70% Sorbitol | 5,00 |
|    | UV-A absorber according to formula (I), employed as a 30% strength solution after neutralization with triethanolamine corresponds to active substance: 3.00% | 10,00 |
| C) | Perfume oil | 0,30 |

Preparation procedure:

Part A: Dissolve Alugel in liquid paraffin with heating. Add the remaining constituents and melt at about 80° C.

Part B: Heat to about 90° C. Add part B to part A with stirring and stir while cooling to room temperature.

Part C: Perfume the cream at about 30° C. and then homogenize.

Example 14

Sunscreen hydrodispersion gel, emulsifier-free

A 30% strength preliminary solution, neutralized with triethanolamine, was prepared of the UV-A absorber according to formula (I). 10% of this preliminary solution was employed, which corresponds to an active content of 3.00% of UV-A absorber in the final formulation.

|    | Constituents | % |
|----|---|---|
| A) | Water, dist. | 75,00 |
|    | Carbopol 1342 | 1,00 |
|    | Triethanolamine | 1,20 |
| B) | UV-A absorber according to formula (I), employed as a 30% strength solution after neutralization with triethanolamine corresponds to active substance: 3.00% | 10,00 |
| C) | Isooctyl p-methoxycinnamate | 3.00 |
|    | Isoamyl p-methoxycinnamate | 3.00 |
|    | Neo Heliopan, type BB | 1.00 |
|    | Isopropyl myristate | 3.00 |
|    | Baysilone oil PK 20 | 2.00 |
|    | Phenonip | 0.50 |
|    | Perfume oil | 0.30 |

Preparation procedure:

Part A: Disperse Carbopol in water in lump-free form and neutralize with triethanolamine.

Part B: Introduce UV-A absorber solution into part A.

Part C: Dissolve Neo Heliopan, type BB in Heliopan, type AV and type E 1000. Add the remaining constituents and add part C to parts A/B with stirring. Then homogenize (colloid mill) and check the pH (7.0–7.5).

Example 15

Sunscreen gel

A 30% strength preliminary solution, neutralized with triethanolamine, was prepared of the UV-A absorber according to formula (I). 13.3% of this preliminary solution was employed, which corresponds to an active content of 4.00% of UV-A absorber in the final formulation.

|    | Constituents | % |
|----|---|---|
| A) | Ethyl alcohol | 5.00 |
|    | Water, dist. | 55.30 |
|    | 1,2-Propylene glycol | 5.00 |
|    | D-Panthenol | 0.50 |
|    | Carbopol ETD 2001 | 1.10 |
| B) | Water | 5.00 |
|    | Triethanolamine | 2.30 |
| C) | Neo Heliopan, type Hydro, employed as a 30% strength solution after neutralization with triethanolamine/phenylbenzimidazolesulphonic acid corresponds to active substance: 3.00% | 10.00 |
|    | UV-A absorber according to formula (I), employed as a 30% strength solution after neutralization with triethanolamine corresponds to active substance: 4.00% | 13.30 |
| D) | Cremophor NP 14 | 1.20 |
|    | Perfume oil | 0.30 |

Preparation procedure:

Part A: Dissolve constituents in the water and disperse Carbopol in lump-free form.

Part B: Dissolve triethanolamine in the water and add part B to part A with stirring.

Part C: Add the sunscreen filter solutions to the gel part A/B with stirring.

Part D: Mix perfume oil with Cremophor and stir in and check pH (7.0–7.5).

Example 16

Sunscreen spray, non-aerosol

A 30% strength preliminary solution, neutralized with triethanolamine, was prepared of the UV-A absorber according to formula (I). 23.35% of this preliminary solution was employed, which corresponds to an active content of 7.00% of UV-A absorber in the final formulation.

|    | Constituents | % |
|----|---|---|
| A) | Ethyl alcohol | 30.00 |
|    | Perfume oil | 0.10 |
| B) | Water, dist. | 39.80 |
|    | Neo Haliopan, type Hydro, employed as a 15% strength solution after neutralization with sodium hydroxide/phenylbenzimidazole-sulphonic acid corresponds to active substance: 1.00% | 6.75 |
|    | UV-A absorber according to formula (I), employed as a 30% strength solution after neutralization with triethanolamine corresponds to active substance: 7.00% | 23,35 |

Preparation procedure:

Part A: Dissolve perfume oil in the alcohol.
Part B: Mix constituents. Add part B to part A and stir.

Example 17

Hair shampoo containing sunscreen

A 30% strength preliminary solution, neutralized with triethanolamine, was prepared of the UV-A absorber according to formula (I). 3.35% of this preliminary solution was employed, which corresponds to an active content of 1.00% of UV-A absorber in the final formulation.

|   | Constituents | % |
|---|---|---|
| A) | Genapol LRO liq. | 18.00 |
|   | Texapon MG 3 | 36.00 |
|   | Lamepon S | 6.00 |
|   | Isoamyl p-methoxycinnamate | 1.00 |
|   | Perfume oil | 0.60 |
| B) | Water dist. | 34.60 |
|   | Euxyl K 100 | 0.15 |
|   | UV-A absorber according to formula (I), employed as a 30% strength solution after neutralization with triethanolamine corresponds to active substance: 1.00% | 3.35 |
|   | Sodium hydroxide, 10% strength in water | 0.10 |
|   | Sodium chloride | 0.20 |

Preparation procedure:

Part A: Mix constituents.

Part B: Dissolve constituents in the water. Add part B to part A with stirring. Stir until a homogeneous product is formed and check pH (7.0–7.5).

Example 18

Hair gel containing sunscreen

A 30% strength preliminary solution, neutralized with triethanolamine, was prepared of the UV-A absorber according to formula (I). 10% of this preliminary solution was employed, which corresponds to an active content of 3.00% of UV-A absorber in the final formulation.

|   | Constituents | % |
|---|---|---|
| A) | Water, dist. | 25.60 |
|   | Glycol 86% | 26.00 |
|   | Carbopol ETD 2001 | 1.50 |
| B) | Water dist. | 3.00 |
|   | Triethanolamine | 3.20 |
| C) | Neo Heliopan, type Hydro, employed as a 30% strength solution after neutralization with triethanolamine/phenylbenzimidazolesulphonic acid corresponds to active substance: 2.00% | 6.70 |
|   | UV-A absorber according to formula (I), employed as a 30% strength solution after neutralization with triethanolamine corresponds to active substance: 3.00% | 10.00 |
|   | Uvinul MS 40 | 1.50 |
|   | Water, dist. | 20.00 |
| D) | Mulsifan RT 203/80 | 1.20 |
|   | Perfume oil | 0.30 |

Preparation procedure:

Part A: Dissolve constituents in the water and disperse Carbopol in lump-free form.

Part B: Dissolve triethanolamine in the water. Add part B to part A with stirring.

Part C: Mix constituents and add to the gel part A/B with stirring.

Part D: Mix the perfume oil with Mulsifan, stir into parts A/B/C and check pH (7.0–7.5).

Example 19

Leave-on hair treatment, transparent, containing sunscreen

A 30% strength preliminary solution, neutralized with triethanolamine, was prepared of the UV-A absorber according to formula (I). 3.35% of this preliminary solution was employed, which corresponds to an active content of 1.00% of UV-A absorber in the final formulation.

|   | Constituents | % |
|---|---|---|
| A) | Water, dist. | 81.50 |
|   | Natrosol 250 HHR | 0.70 |
|   | Ethyl alcohol | 5.00 |
|   | Uvinul P 25 | 5.00 |
|   | UV-A absorber according to formula (I), employed as a solution after neutralization with triethanolamine corresponds to active substance: 1.00% | 3.35 |
| B) | Nutrilan L | 2.00 |
|   | Dehyquart A | 0.20 |
|   | Phenonip | 0.50 |
|   | Triethanolamine | 0.25 |
| C) | Mulsifan RT 203/80 | 1,20 |
|   | Perfume oil | 0,30 |

Preparation procedure:

Part A: Heat water to about 85° C. Sprinkle in Natrosol and cool to room temperature with vigorous stirring. Add remaining constituents.

Part B: Weigh into part A and stir.

Part C: Mix Mulsifan with the perfume oil, add to part A/B, stir well and check the pH (7.0–7.5).

We claim:

1. In a sunscreen composition containing a UV absorber, the improvement wherein such UV absorber has its absorption maximum in the UV-A range, and per molecule contains at least two benzazolyl groups and at least one $SO_3Y$ group in which Y is hydrogen, Li, Na, K, $NH_4$, ½Ca, ½Mg, ⅓Al or the cation of an organic nitrogen base.

2. A sunscreen composition according to claim 1, wherein the UV absorber is of the formula $$\left[ R^1_p\text{--}Z_m\text{--}C \begin{array}{c} N \\ \diagup \diagdown \\ X \end{array} \begin{array}{c} R^2 \\ R^3 \\ R^4 \\ R^5 \end{array} \right]_n \quad (I)$$

in which

Z is a (n+p)-valent organic radical having one or more double bonds in such a position that they complete the double bond systems of at least 2 of the bracketed radicals to give a conjugated total system, and X is S, O or $NR^6$, $R^1$ is hydrogen, $C_1$–$C_{18}$-alkyl, $C_1$–$C_4$-alkoxy, $C_5$–$C_{15}$-aryl, $C_2$–$C_{18}$-acyloxy, $SO_3Y$ or COOY, $R^2$ to $R^5$ independently of one another denote nitro or the meaning indicated under $R^1$, $R^6$ is hydrogen, $C_1$–$C_4$-alkyl or hydroxy-$C_1$–$C_4$-alkyl, Y is hydrogen, Li, Na, K. NH$_4$, ½Ca, ½Mg, ⅓Al or the cation of an organic nitrogen base employed for the neutralization of the free acid groups, p is an integer from 0 to 4, m is 0 or 1, n is an integer from 2 to 6, and n+p is at most 6, the UV absorber containing at least one SO$_3$Y group.

3. A sunscreen composition according to claim 2, in which Z is
- a) an olefinically unsaturated aliphatic C$_2$–C$_6$-hydrocarbon radical which can be interrupted by a C$_5$–C$_{12}$-arylene radical or a C$_4$–C$_{10}$-hetarylene radical,
- b) a C$_5$–C$_{15}$-arylene radical which can be interrupted by an olefinically unsaturated aliphatic C$_2$–C$_6$-hydrocarbon radical, or
- c) a C$_3$–C$_{10}$-hetarylene radical, each of the radicals under a), b) and c) being optionally substituted by at least one member selected from the group consisting of C$_1$–C$_6$-alkyl, C$_1$–C$_6$-alkoxy, phenoxy, hydroxyl, or a methylenedioxy or amino group which itself is optionally substituted by 1 or 2 C$_1$–C$_5$-alkyl radicals.

4. A sunscreen composition according to claim 2, in which Z is selected from the group consisting of —CH=CH—, —CH=CH—CH=CH—,

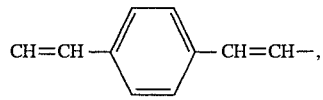

phenylene, biphenylene, naphthylene,

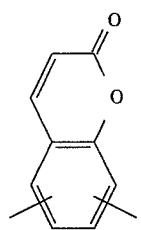

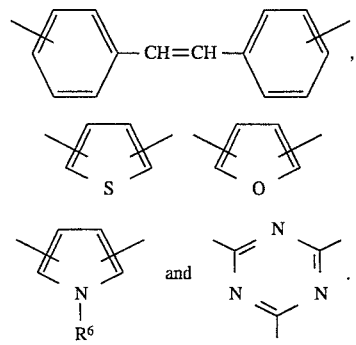

5. A sunscreen composition according to claim 4, in which X is NR$^6$.

* * * * *